United States Patent [19]

Hainaut et al.

[11] 4,028,386

[45] June 7, 1977

[54] NOVEL β-KETONE COMPOUNDS

[75] Inventors: Daniel Hainaut, Villemomble; Jean-Pierre Demoute, Montreuil-sous-Bois, both of France

[73] Assignee: Roussel-UCLAF, Paris, France

[22] Filed: Sept. 3, 1974

[21] Appl. No.: 502,635

[30] Foreign Application Priority Data

Sept. 24, 1973 France .................. 73.34076

[52] U.S. Cl. .................. 260/410.9 R; 260/483; 260/484 R; 260/484 A
[51] Int. Cl.² .................. C11C 3/02; C07C 69/66
[58] Field of Search ............ 260/410.9 R, 410.9 N, 260/483, 484 R, 484 A, 405 S, 406

[56] References Cited

UNITED STATES PATENTS

| | | | |
|---|---|---|---|
| 2,870,208 | 1/1959 | Guex | 260/483 |
| 3,156,714 | 11/1964 | Surmatis | 260/410.9 R |
| 3,565,928 | 2/1971 | Hagarty | 260/410.9 R |
| 3,775,467 | 11/1973 | Greth | 260/483 |

OTHER PUBLICATIONS

Chemical Abstracts, 72:42700v.
Chemical Abstracts, 76:72104d.

*Primary Examiner*—Winston A. Douglas
*Assistant Examiner*—John F. Niebling
*Attorney, Agent, or Firm*—Hammond & Littell

[57] ABSTRACT

Novel β-ketone compounds of the formula

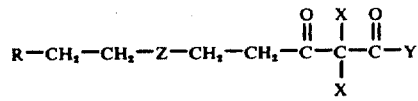

wherein R is a linear or branched alkyl of 4 to 10 carbon atoms optionally containing a double bond or an epoxy and optionally substituted with a branched or linear alkoxy of 1 to 3 carbon atoms, Z is selected from the group consisting of —CH=CH—, —CHOH—CH=CH—,

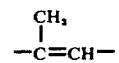

and —OCH$_2$—, X is selected from the group consisting of hydrogen and methyl, Y is selected from the group consisting of linear and branched alkoxy of 1 to 5 carbon atoms and

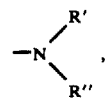

and R' and R'' are linear or branched alkyl of 1 to 4 carbon atoms which are insecticides and their preparation.

7 Claims, No Drawings

NOVEL β-KETONE COMPOUNDS

OBJECTS OF THE INVENTION

It is an object of the invention to provide the novel β-ketones of formula I.

It is another object of the invention to provide a novel process for the preparation of compounds of formula I and novel intermediates therefor.

It is a further object of the invention to provide novel insecticidal compositions and a novel method of killing insects.

These and other objects and advantages of the invention will become obvious from the following detailed description.

THE INVENTION

The novel products of the invention have the formula

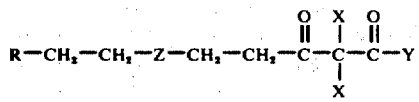

wherein R is a linear or branched alkyl of 4 to 10 carbon atoms optionally containing a double bond or an epoxy and optionally substituted with a branched or linear alkoxy of 1 to 3 carbon atoms, Z is selected from the group consisting of —CH=CH—, —CHOH—CH=CH—,

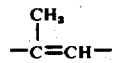

and —OCH$_2$—, X is selected from the group consisting of hydrogen and methyl, Y is selected from the group consisting of linear and branched alkoxy of 1 to 5 carbon atoms and

and R' and R'' are linear or branched alkyl of 1 to 4 carbon atoms.

Examples of suitable compounds of formula I are those where R is butyl, isobutyl, pentyl, isopentyl, hexyl, isohexyl, heptyl, isoheptyl, octyl, isooctyl, nonyl and decyl and Y is alkoxy such as methoxy, ethoxy, propoxy, iospropoxy, butoxy, isobutoxy and pentoxy, R' and R'' may be alkyl such as methyl, ethyl, propyl, isopropyl or butyl.

The most preferred compounds of formula I are those where R is branched or linear alkyl of 4 to 5 carbon atoms optionally containing a double bond or an epoxy and optionally substituted with methoxy, Z is —CH=CH—, —CHOH—CH=CH—,

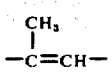

or —OCH$_2$—, X is hydrogen or methyl and Y is branched or linear alkoxy of 1 to 3 carbon atoms or

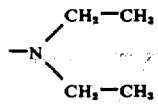

The novel compounds of formula I may be prepared by reacting a compound of the formula

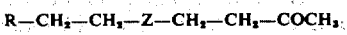

wherein R and Z have the above definitions except R may not contain an epoxy with an alkyl carbonate of the formula

wherein R$_2$' is branched or linear alkyl of 1 to 5 carbon atoms in the presence of an alkaline agent to form a compound of the formula

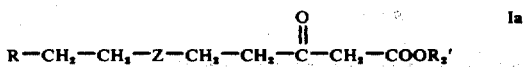

corresponding to compounds of formula I in which Y is linear or branched alkoxy and X is hydrogen which may be reacted if desired either with an organic peracid when R has a double bond to obtain the corresponding products of formula I wherein Y is branched or linear alkoxy, X is hydrogen and R has an epoxy or with one of the formula

wherein R' and R'' have the above definitions to obtain a compound of the formula

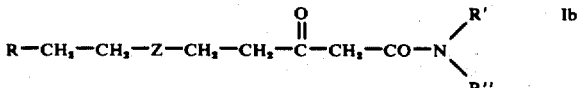

which corresponds to compounds of formula I where Y is

and X is hydrogen. The latter product may be reacted with an organic peracid when R has a double bond to obtain compounds of formula I wherein Y is

X is hydrogen and R has an epoxy.

The compounds of formula Ia may also be reacted with a methylation agent in the presence of an alkaline agent to obtain a compound of the formula

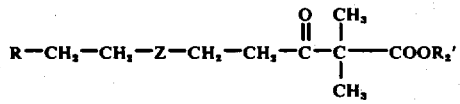

wherein $R_2'$ and Z and R have the above definitions which corresponds to compounds of formula I wherein Y is branched or linear alkoxy and X is methyl and when R has a double bond, the product of formula Ic may be reacted with an organic peracid to form the corresponding compounds of formula I wherein Y is branched or linear alkoxy, X is methyl and R has an epoxy function.

It is also possible to combine certain possibilities of the process such as reacting a compound of formula Ic with an amine of the formula

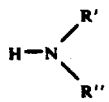

to form compounds of the formula

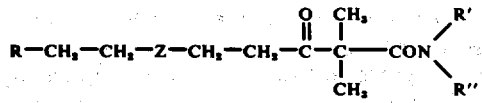

which corresponds to compounds of formula I wherein Y is

and X is methyl and optionally treating the latter with an organic peracid when R has a double bond to obtain the corresponding compound of formula I wherein Y is

X is methyl and R contains an epoxy.

The alkaline agent present in the reaction of the ketone of formula II with the alkyl carbonate is preferably sodium hydride but equally useful are alkali metal amides such as sodium amide or potassium amide or an akali metal alcoholate such as sodium methylate or potassium tert.-butylate. The organic peracid to form the epoxy is preferably m-chloroperbenzoic acid but equally useful are monoperphthalic acid, p-nitroperbenzoic acid, peracetic acid or trifluoroperacetic acid.

The alkaline agent used for the methylation of compounds of formula Ia is preferably sodium methylate but equally useful are other alkali metal alcoholates such as sodium ethylate or potassium tert.-butylate.

A modification of the process of the invention comprises reacting a compound of the formula

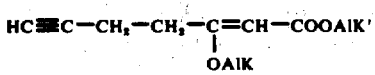

wherein AlK and AlK' are branched or linear alkyl of 1 to 4 carbon atoms with an aldehyde of the formula

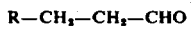

wherein R has the above definition except it does not contain an epoxy in the presence of a salt or organic derivative of an alkali metal and selectively reducing the resulting acetylenic product to the ethylenic product with hydrogen in the presence of a conventional catalyst to obtain a compound of the formula

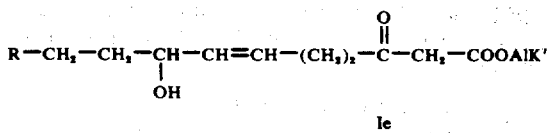

corresponding to compounds of formula I wherein Z is —CHOH—CH=CH—, Y is alkoxy and R is as defined above without the presence of an epoxy.

The alkali metal derivative to react with the product of formula IV is preferably butyl lithium but equally useful are alklai metal hydrides or amides such as sodium hydride or sodium amide. The selective hydrogenation catalyst is preferably palladized barium sulfate but equally useful are palladized calcium carbonate or Raney Nickel.

The double bond present in certain compounds of formula I can have its substituents in different forms, E isomer, Z isomer and mixtures thereof.

The insecticidal compositions of the invention are comprised of an effective amount of at least one compound of formula I and an insecticidal carrier and can contain one or more other pesticidal agents. The compositions may be in the form of powders, granules, suspensions, emulsions, aerosol solutions, baits or any other preparation classically used for insecticides. The concentration of the active ingredient may vary widely but is usually 0.001 to 5%, preferably 0.005 to 2%, by weight of the composition.

Besides the active component, the compositions generally contain a vehicle and/or non-ionic surface active agent to assure a uniform dispersion of the materials making up the composition. The vehicle may be a liquid such as water, alcohol, hydrocarbons or other organic solvents or a mineral, vegetable or animal oil or a powder such as talc, clays, silicates, Kieselguhr, etc.

An example of a suitable emulsifiable concentrate of the invention consists of 0.1% by weight of methyl 10-epoxy-7,11-dimethyl-3-oxo-6-dodecenoate, 5% by weight of Polysorbate 80 [polyoxyethylene (20) sorbitan monooleate], 94.8% by weight of xylene and 0.1% by weight of Topanol A (2,4-dimethyl-6-tertbutylphenol).

The insecticidal compositions of the invention have remarkable properties and are especially active against the eggs, larvae and pupa but are equally effective against adult insects. When the larvae form of the insects is treated with the insecticidal composition of the invention, larvae evolution is incomplete resulting in the formation of giant larvae possessing malformations and generally not resulting in normal adult forms. When the larvae do rarely form an adult of normal appearance, the insect is sterile.

The novel method of the invention for combatting insects comprises contacting insects with an insecticidally effective amount of a compound of formula I. The insect, as noted above may be in any stage of growth.

Another aspect of the invention are the following novel intermediate products, 10-methyl-6-oxa-9-undecene-2-one, 2-oxo-5-(Z)-tridecene and 10-methoxy-6,10-dimethyl-5-undecene-2-one.

In the following examples there are described several preferred embodiments to illustrate the invention. However, it should be understood that the invention is not intended to be limited to the specific embodiments.

EXAMPLE 1

Methyl 11-methyl-7-oxa-3-oxo-10-dodecenoate

STEP A:

2,2-ethylenedioxy-10-methyl-6-oxa-9-undecene 14 g of sodium hydride in a 50% suspension in oil were added to a solution of 28 g of 4-methyl-3-pentenol [Julia et al, Bull. Soc. Chim., (1960), p. 1072] in 250 ml of dimethylformamide and after stirring the mixture for 1 hour, 66 g of 5-bromo-2,2-ethylenedioxy-pentane were added thereto while keeping the temperature below 35° C. The mixture was stirred at room temperature for 17 hours and the reaction mixture was then poured into water. The mixture was extracted with petroleum ether (b.p. = 40°–75° C) and the organic phase was washed with water, dried over sodium sulfate and evaporated to dryness. The residue was rectified to obtain 20 g of 2,2-ethylenedioxy-10-methyl-6-oxa-9-undecene in the form of a colorless liquid with a boiling point of 75° C at 0.05 mm Hg.

STEP B: 10-methyl-6-oxa-9-undecene-2-one

A suspension of 19.7 g of the product of Step A in 100 ml of acetone containing 200 ml of 0.1N hydrochloric acid was stirred at room temperature for 17 hours and the acetone was then evaporated under reduced pressure. The mixture was then extracted with methylene chloride and the organic solution was washed with aqueous sodium bicarbonate solution, then with water, dried over sodium sulfate and evaporated to dryness to obtain 15.7 g of 10-methyl-6-oxa-9-undecene-2-one in the form of a colorless liquid used as is for the next step.

STEP C: Methyl 11-methyl-7-oxa-3-oxo-10-dodecenoate

A solution of 6.5 g of the product of Step B in 10 ml of ethyl ether was added to a mixture of 3.4 g of sodium hydride in a 50% oil suspension and 30 ml of ethyl ether containing 40 ml of methyl carbonate and the mixture was refluxed for three hours and cooled. The mixture was poured into water and the mixture was acidified by addition of 1N hydrochloric acid. The ether phase was decanted and the aqueous phase was extracted with methylene chloride. The combined organic phases were washed with an aqueous sodium bicarbonate solution, then with water, dried over sodium sulfate and the ether was evaporated. The residue was chromatographed over silica and was eluted with a 7-3 mixture of petroleum ether (b.p. of 40°–75° C) and ethyl acetate to obtain 5.4 g of methyl 11-methyl-7-oxa-3-oxo-10-dodecenoate with form of a colorless oil with a refractive index $n_D^{25} = 1.4580$.

Analysis: $C_{13}H_{22}O_4$: Calculated: %C 64.44 %H 9.15, Found: %C 64.5 %H 8.9.

EXAMPLE 2

Methyl 10-epoxy-11-methyl-7-oxa-3-oxo-dodecanoate 3 g of the final product of Example 1 were dissolved in 30 ml of methylene chloride and a solution of 2.3 g of m-chloroperbenzoic acid in 50 ml of methylene chloride was added dropwise thereto at −5° C. The mixture was stirred at −5° C for 5 minutes and then was poured into 100 ml of a aqueous saturated sodium bicarbonate solution. The organic phase was decanted and the aqueous phase was extracted with methylene chloride. The combined organic phases were washed with water, dried over sodium sulfate and evaporated to dryness under reduced pressure. The residue was chromatographed over silica and was eluted with a 9-1 benzene-ethyl acetate mixture to obtain 2.9 g of methyl 10-epoxy-11-methyl-7-oxa-3-oxo-dodecanoate in the form of a colorless oil with a refractive index $n_D^{25} = 1.4514$.

Analysis: $C_{13}H_{22}O_5$: Calculated: %C 60.44 %H 8.59, Found: %C 60.3 %H 8.5.

EXAMPLE 3

Methyl 7,11-dimethyl-3-oxo-6,10-dodecadienoate

Ether was distilled from a mixture of 9.6 g of sodium hydride in a 50% oil suspension, 50 ml of ethyl ether, 20 ml of methyl carbonate and 19.4 g 6,10-dimethyl-2-oxo-5,9-undecadiene (40% Z isomer - 60% E isomer) which was replaced with benzene and when the distillation temperature reached 65° C, the mixture was refluxed for 1 hour. The reaction mixture was poured into water containing ammonium chloride and the mixture was extracted with methylene chloride. The organic phase was washed with water, dried over sodium sulfate and evaporated to dryness under reduced pressure. The residue was chromatographed over silica and was eluted with a 9-1 benzene-ethyl acetate mixture to obtain 20 g of methyl, 7,11-dimethyl-3-oxo-6,10-dodecadienoate in the form of a yellow oil. The product was a mixture of the horizontal E and Z isomers of the double bond at the 6-position.

Analysis: $C_{15}H_{24}O_3$: Calculated: %C 71.39 %H 9.59, Found: %C 71.4 %H 9.7.

EXAMPLE 4

Methyl 10-epoxy-7,11-dimethyl-3-oxo-6-dodecenoate

A solution of 5.1 g of m-chloroperbenzoic acid in 50 ml of methylene chloride was added dropwise at −40° C under a nitrogen atmosphere to a solution of 6 g of the product of Example 3 in 60 ml of methylene chloride and after stirring for 15 minutes at −20° C, the mixture was poured into a saturated aqueous sodium bicarbonate solution. The mixture was extracted with methylene chloride and the organic phase was washed with aqueous sodium bicarbonate solution and then with water, dried over sodium sulfate and evaporated to dryness under reduced pressure. The residue was chromatographed over silica and was eluted with a 7-3 benzene-ethyl acetate mixture to obtain 3.1 g of methyl 10-epoxy-7,11-dimethyl-3-oxo-6-dodecenoate in the form of a colorless liquid with a refractive index $n_D^{25} = 1.4680$.

Analysis: $C_{15}H_{24}O_4$: Calculated: %C 67.15 %H 9.02; Found: %C 67.4 %H 9.0.

EXAMPLE 5

Ethyl 8-hydroxy-3-oxo-6-tetradecenoate

STEP A: Ethyl 8-hydroxy-3-oxo-6-tetradecynoate 37 ml of a hexane solution of 1N butyl lithium were added under a nitrogen atmosphere to a solution of 10 g of ethyl 3-ethoxy-6-yne-2-heptenoate in 75 ml of tetrahydrofuran cooled to −60° C and the mixture was stirred for 2 hours at −60° C. 6.9 g of heptanal were then added and after stirring for another hour at −60° C, the mixture was allowed to return to room temperature. The mixture was poured into an aqueous monosodium phosphate solution and the organic phase was decanted. The aqueous phase was extracted with ethyl acetate and the combined organic phases were washed with aqueous sodium bicarbonate, with water, dried over magnesium sulfate and evaporated to dryness. The resulting yellow oil was dissolved in 120 ml of ethanol containing 60 ml of 2N hydrochloric acid and the mixture was stirred under a nitrogen atmosphere at room temperature for 16 hours. The mixture was poured into water and was extracted with methylene chloride. The organic extracts were dried over magnesium sulfate and evaporated to dryness under reduced pressure to obtain a yellow oil which was chromatographed over silica and eluted with a 8-2 methylene chloride-ethyl acetate mixture to obtain 6 g of ethyl 8-hydroxy-3-oxo-6-tetradecyanoate as a yellow oil with a refractive $n_D^{23}$ = 1.4705.

STEP B: ethyl 8-hydroxy-3-oxo-6-tetradecenoate

A solution of 10 g of the product of Step A in 50 ml of ethyl acetate containing 1 ml of quinoline was added to a suspension of 1 g of 50% palladized barium sulfate in 50 ml of ethyl acetate and the mixture was stirred in a hydrogen atmosphere until absorption ceased. The catalyst was removed by filtration and the filtrate was washed with dilute hydrochloric acid and water, dried over magnesium sulfate and evaporated. The residue was chromatographed over silica and was eluted with an 8-2 mixture of methylene chloride-ethyl acetate to obtain 6 g of ethyl 8-hydroxy-3-oxo-6-tetradecenoate in the form of a pale yellow oil with a refractive index of $n_D^{23}$ = 1.4602.

Analysis: $C_{16}H_{28}O_4$: Calculated: %C 67.56 %H 9.92; Found: %C 67.9 %H 10.2.

EXAMPLE 6

Ethyl 3-oxo-6-(Z)-tetradecenoate

STEP A: 2,2-ethylenedioxy-5-(Z)-tridecene

A solution of 4.5 g of potassium tert.-butylate in 300 ml of dimethylformamide was added to a mixture of 18.8 g of triphenyl 2,2-ethylenedioxy-pentyl phosphonium bromide [Machleidt et al, Ann. Chem., Vol. 690 (1965), p. 79], 5.1 g of octanal and 200 ml of dimethylformamide cooled to −45° C and after stirring for 15 minutes, the mixture was poured into water. The mixture was extracted with ether and the ether extracts were washed with water, dried over sodium sulfate and evaporated to dryness to obtain 9.6 g of 2,2-ethylenedioxy-5 (Z)-tridecene in the form of an amber oil which was used as is for the next step.

STEP B: 2-oxo-5(Z)-tridecene

A solution of 9.6 g of the product of Step A in 160 ml of ethanol containing 100 ml of 0.5N hydrochloric acid was stirred for 16 hours at room temperature and then the ethanol was evaporated under reduced pressure. The mixture was extracted with ether and the ether extract was washed with water, with a saturated aqueous sodium bicarbonate solution, with water, dried over sodium sulfate and evaporated to dryness to obtain 6.9g of 2-oxo-5(Z)-tridecene in the form of a pale yellow oil which was used as is in the next step.

STEP C: Ethyl 3-oxo-6(Z)-tetradecenoate 6.85 g of the product of Step B were added to 2 g of sodium hydride in a 50% oil suspension in 35 ml of ethyl ether and after stirring the mixture for 15 minutes, 6.2 g of ethyl carbonate were added thereto. Benzene was added thereto and the ether was evaporated. The mixtue was then refluxed for 1½ hours, cooled and poured into water. The mixture was decanted and the organic phase was washed with dilute hydrochloric acid, with a saturated aqueous sodium bicarbonate solution, with water, dried over sodium sulfate and evaporated to dryness. The residue was chromatographed over silica and was eluted with a 9-1 pertroleum ether (b.p. = 40°–75° C)-ethyl ether mixture to obtain 1.74 g of ethyl 3-oxo-6(Z)-tetradecenoate in the form of a colorless oil with a refractive index of $n_D^{20}$ = 1.4596.

Analysis: $C_{16}H_{28}O_3$: Calculated: %C 71.60 %H 10.52, Found: %C 71.7 %H 10.4.

The IR spectra on the products in each stage indicated the double bond was a Z structure.

EXAMPLE 7

Methyl 10-epoxy-2,2,7,11-tetramethyl-3-oxo-6-dodecenoate

STEP A: Methyl 2,2,7,11-tetramethyl-3-oxo-6,10-dodecadienoate

A mixture of 1.14 g of 95% sodium methylate and 2.52 g of the final product of Example 3 in 20 ml of methanol was stirred for 10 minutes and after the addition of 2.84 g of methyl iodide, the mixture was stirred for 16 hours at room temperature. The mixture was refluxed for 4 hours and the methanol was evaporated and water was added. The mixture was extracted with methylene chloride and the extracts were washed with water, dried over sodium sulfate and evaporated to dryness. The residue was chromatographed over silica and was eluted with a 9-1 pertroleum ether (b.p. = 40°–75° C)-ethyl ether mixture to obtain 1.37 g of methyl 2,2,7,11-tetramethyl-3-oxo-6,10-dodecadienoate in the form of a colorless oil with a refractive index of $n_D^{17}$ = 1.470.

STEP B: Methyl 10-epoxy-2,2,7,11-tetramethyl-3-oxo-6-dodecenoate

A solution of 1.32 g of m-chloroperbenzoic acid in 50 ml of methylene chloride was added to a solution of 1.93 g of the product of Step A in 50 ml of methylene chloride cooled to −50° C and the mixture was stirred for 1 hour at −40° C and 2½ hours at −5° C. The mixture was poured into a saturated aqueous sodium bicarbonate solution and the organic phase was decanted. The aqueous phase was extracted with methylene chloride and the combined organic phases were washed with water, dried over sodium sulfate and evaporated to dryness. The residue was chromatographed over silica and was eluted with a 95-5 mixture of benzene and ethyl acetate to obtain 0.88 g of methyl 10-epoxy- 2,2,7,11-tetramethyl-3-oxo-6-dodecenoate in the form of a colorless oil.

Analysis: $C_{17}H_{28}O_4$: Calculated: %C 68.89 %H 9.52; Found: %C 68.9 %H

EXAMPLE 8

Ethyl 10-epoxy-7,11-dimethyl-3-oxo-6-dodecenoate

STEP A: Ethyl 7,11-dimethyl-3-oxo-6,10-dodecadienoate 9.45 g of diethyl carbonate and 7.8 g of 6,10-dimethyl-2-oxo-5,9-undecadiene were added to a suspension of 3.84g of sodium hydride in a 50% oil suspension in 40 ml of benzene and the mixture was refluxed for 2½ hours and then cooled. The mixture was poured into dilute hydrochloric acid and was then extracted with ethyl acetate. The organic phase was washed with water, dried over sodium sulfate and evaporated to dryness. The residue was chromatographed over silica and was eluted with benzene to obtain 3.96 g of ethyl 7,11-dimethyl-3-oxo-6,10-dodecadienoate in the form of a yellow oil which was used as is for the next step.

STEP B: Ethyl 10-epoxy-7,11-dimethyl-3-oxo-6-dodecenoate

A solution of 2.59 g of m-chloroperbenzoic acid in 50 ml of methylene chloride was added to a solution of 3.6 g of the product of Step A in 50 ml of methylene chloride cooled to $-50°$ C and the mixture was held at $-5°$ C for 1 hour and was then poured into a saturated aqueous sodium bicarbonate solution. The organic phase was decanted and the aqueous phase was extracted with methylene chloride. The organic extracts were washed with water, dried over sodium sulfate and evaporated to dryness. The residue was chromatographed over silica and was eluted with a 7-3 benzene-ethyl acetate mixture to obtain 2.2 g of ethyl 10-epoxy-7,11-dimethyl-3-oxo-6-dodecenoate in the form of a pale yellow oil with a refractive index of $n_D^{22} = 1.4662$.

Analysis: $C_{16}H_{26}O_4$: Calculated: %C 68.06 %H 9.28; Found: %C 68.4; 9.4.

EXAMPLE 9

Isopropyl 10-epoxy-7,11-dimethyl-3-oxo-6-dodecenoate

STEP A: isopropyl 7,11-dimethyl-3-oxo-6,10-dodecadienoate

A solution of 1.92 g of sodium hydride in 200 ml of isopropanol was added to a boiling mixture of 10 g of the product of Example 3 and 200 ml of isopropanol and the volume was held constant by replacing proportionately the distillate with isopropanol for 2 hours. After cooling, the mixture was poured into water and acidified with concentrated hydrochloric acid. The mixture was extracted with ethyl acetate and the extract was washed with water, dried over sodium sulfate and evaporated to dryness. The residue was chromatographed over silica and was eluted with a 9-1 petroleum ether (b.p. = $40°-75°$ C)-ethyl ether mixture to obtain 7.05 g of isopropyl 7,11dimethyl-3-oxo-6,10-dodecadienoate in the form of an amber oil with a refractive index of $n_D^{24} = 1.467$.

STEP B: isopropyl 10-epoxy-7,11-dimethyl-3-oxo-6-dodecenoate

Using the procedure of Step B of Example 8, 5.6 g of the product from Step A were reacted to form a product which was chromatographed over silica and was eluted with an 8–2 benzene-ethyl acetate mixture to obtain 3.37 g of isopropyl 10-epoxy-7,11-dimethyl-3-oxo-6-dodecenoate in the form of a pale yellow oil with a refractive index of $n_D^{24} = 1.462$ Analysis: $C_{17}H_{28}O_4$: Calculated: %C 68.89 %H 9.52; Found: %C 68.5 %H 9.5.

EXAMPLE 10

N,N-diethyl-10-epoxy-7,11-dimethyl-3-oxo-6-dodecenamide

STEP A: N,N-diethyl-7,11-dimethyl-3-oxo-6,10-dodecadienamide 5.4 g of the product of Example 3 and 10.8ml of diethylamine were stirred in a closed auto clave at 110° C for 70 hours and after cooling, the reaction mixture was recovered and evaporated under reduced pressure. The residue was chromatographed over silica and was eluted with a 1-1 ethyl etherpetroleum ether (b.p. = $40°-75°$ C) mixture to obtain 3.6 g of N,N-diethyl-7,11-dimethyl-3-oxo-6,10-dodecadienamide in the form of an orange oil.

Analysis: $C_{18}H_{31}NO_2$. Calculated: %C 73.68 %H 10.65 %N 4.77; Found: %C 73.8 %H 10.8 %N 4.5.

STEP B: N,N-diethyl-10-epoxy-7,11-dimethyl-3-oxo-6-dodecenamide

Using the procedure of Step B of Example 8, 2 g of the product of Step A were reacted to form a product which was chromatographed over silica and was eluted with a 6-4 benzeneethyl acetate mixture to obtain 0.5 g of N,N-diethyl-10-epoxy-7,11-dimethyl-3-oxo-6-dodecenamide in the form of a yellow oil.

Analysis: $C_{18}H_{31}NO_3$: Calculated: %C 69.86 %H 10.11 %N 4.53; Found: %C 69.6 %H 10.4 %N 4.4.

EXAMPLE 11

Methyl 11-methoxy-7,11-dimethyl-3-oxo-6-dodecenoate

STEP A: 2,2-ethylenedioxy-10-methoxy-6,10-dimethyl-5-undecene 8.15 g of potassium tert.-butylate were added to a solution of 38 g of triphenyl 2,2-ethylenedioxy-pentyl phosphonium bromide in 400 ml of dimethylformamide cooled to 0° C and then 12.75 g of 6-methoxy-6-methyl-2-heptanone were added. The mixture was stirred for 4 hours at 0° C and was then poured into water. The mixture was extracted with petroleum ether (b.p. = $40°-75°$ C) and the extracts were washed with water, dried over sodium sulfate and evaporated to dryness. The yellow oil was chromatographed over silica and was eluted with a 8-2 benzene-ethyl acetate mixture to obtain 9.15 g of 2,2-ethylenedioxy-10-methoxy-6,10-dimethyl-5-undecene in the form of a colorless oil which was a mixture of the E and Z isomers with respect to the double bond in the 5-position. A supplementary chromatography under pressure and elution with a 9-1 benzene-ethyl acetate mixture gave a separation of the E and Z isomers.

STEP B: 10-methoxy-6,10-dimethyl-5-undecene-2-one

This and the next reaction could be effected with the E and Z isomers or mixtures thereof. A solution of 1.1 g of 2,2-ethylenedioxy-10-methoxy-6,10-dimethyl-5-undecene in 22 ml of methanol containing 11 ml of 0.5N aqueous hydrochloric acid was stirred for 20 hours at room temperature and was then diluted with water and extracted with petroleum ether (b.p. = 40°–75° C). The extracts were washed with an aqueous sodium bicarbonate solution, then with water and evaporated to dryness to obtain 900 mg of 10-methoxy-6,10-dimethyl-5-undencene-2-one in the form of a colorless oil which was used as is for the next step.

STEP C: Methyl 11-methoxy-7,11-dimethyl-3-oxo-6-dodecenoate

A mixture of 900 mg of the product from Step B, 1 ml of methyl carbonate and 15 ml of dimethylformamide was heated to 40° C and 360 mg of sodium hydride in a 50% oil suspension were added thereto portion wise and the mixture was stirred for 6 hours at room temperature. The mixture was poured into an aqueous hydrochloric acid solution and was extracted with petroleum ether (b.p. = 40°–75° C). The extracts were washed with water, dried over sodium sulfate and evaporated to dryness. The residue was chromatographed over silica and was eluted with a 7–3 pertroleum ether-ethyl ether mixture to obtain 374 mg of methyl 11-methoxy-7,11-dimethyl-3-oxo-6-dodecenoate in the form of a colorless oil.

The product can be obtained in the form of a mixture of E and Z isomers by adding dropwise 3 ml of concentrated sulfuric acid to a solution of 7.6 g of the product of Example 3 in 45 ml of methanol and stirring the mixture at room temperature for 40 hours. The mixture was diluted with water and extracted with methylene chloride. The extracts were washed with water, dried over sodium sulfate and evaporated to dryness and the residue was chromatographed over silica and was eluted with a 9-1 benzene-ethyl acetate mixture to obtain 1.3 g of methyl 11-methoxy-7,11-dimethyl-3-oxo-6-dodecenoate in the form of a colorless oil.

INSECTICIDAL ACTIVITY

A. Larvae of Dysdercus intermedius and nymphs of tenebrio molitor

The test was effected of larvae nearing the last stage of their development and a topical application of 5 µl of an acetone solution of 20 and 2 g/liter of test product was made to the abdominal tergites of the insects which is a dose of 100 and 10 µg of product per insect. 10 insects were used for each dose and at the end of the test which is when the control larvae not having been subjected to any treatment have become adult individuals, each of the treated larvae were noted on a scale of 0 to 5. The value 0 corresponds to an adult individual of normal appearance and the value 5 corresponds to a giant larvae which has not grown into an adult or a second nymph and the intermediate values correspond to individuals more or less complete and resulting in one or more abnormal forms. The results of Table I are the average of 10 insects at each dose and the average of values obtained on non-treated larvae are always very near to 0.

TABLE I

| Product of Example | Dysdercus intermedius 100 µg | 10 µg | Tenebrio molitor 100 µg | 10 µg |
|---|---|---|---|---|
| 5 | 4.7 | 0 | — | — |
| 6 | 3.7 | 0 | 2.9 | 2 |
| 3 | 4.2 | 0.1 | — | — |

TABLE I-continued

| Product of Example | Dysdercus intermedius 100 µg | 10 µg | Tenebrio molitor 100 µg | 10 µg |
|---|---|---|---|---|
| 4 | 5 | 4.6 | 3.4 | 2.6 |

B. Aedes aegypti larvae

The preceding acetone solutions were used in this test by direct addition to water where the larvae of Aedes aegypti are produced and the doses used were 10 and 1 ppm of the test product. The results expressed as percentage of mortality of the larvae are in Table II.

TABLE II

| Product of Example | % mortality 10 ppm | 1 ppm |
|---|---|---|
| 6 | 20 | — |
| 3 | 30 | — |
| 4 | 70 | 10 |

C. Eggs of Dysdercus intermedius

A piece of filter paper measuring 15 × 6 cm was impregnated with an acetone solution of the test products corresponding to 0.1, 1 and 10 g per m² of filter paper surface and the pieces of filter paper were placed in a ring about the interior face of a beaker containing 2 adult couples of Dysdercus intermedius. The laid eggs, fixed on the filter paper, were recovered and placed in an incubator. The percentage of eggs not hatching was determined for each dose of the product and the results are reported in Table III.

TABLE III

| Product of Example | % not hatching - dose in g/m² 0.1 | 1.0 | 10 |
|---|---|---|---|
| 5 | 95 | — | — |
| 6 | 50 | 73 | — |
| 3 | 26 | 100 | — |
| 4 | — | — | 100 |
| 1 | 30 | 67 | — |
| 2 | 68 | 100 | — |

The results of Tables I to III show the insecticidal effectiveness of the tested products.

Various modifications of the product and method of the invention may be made without departing from the spirit or scope thereof and it is to be understood that the invention is to be limited only as defined in the appended claims.

I claim:

1. A compound of the formula

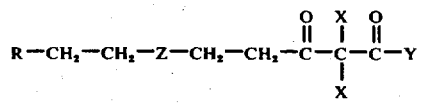

wherein R is a linear or branched alkyl of 4 to 10 carbon atoms, linear or branched alkenyl of 4 to 10 carbon atoms and alkoxyalkyl of 5 to 13 carbon atoms Z is selected from the group consisting of —CH=CH—, —CHOH—CH=CH—,

and —OCH$_2$—, X is selected from the group consisting of hydrogen and methyl, Y is linear and branched alkoxy of 1 to 5 carbon atoms.

2. A compound of claim 1 wherein R is a branched or linear alkyl of 4 to 5 carbon atoms branched or linear, alkenyl of 4 to 5 carbon atoms and methoxy alkyl of 4 to 5 alkyl carbon atoms and Y is branched or linear alkoxy of 1 to 3 carbon atoms.

3. A compound of claim 1 is methyl 11-methyl-7-oxa-3-oxo-10-dodecenoate.

4. A compound of claim 1 which is methyl 7,11-dimethyl-3-oxo-6,10-dodecadienoate.

5. A compound of claim 1 which is ethyl 8-hydroxy-3-oxo-6-tetradecenoate.

6. A compound of claim 1 which is ethyl 3-oxo-6(Z)-tetradecenoate.

7. A compound of claim 1 which is methyl 11-methoxy-7,11-dimethyl-3-oxo-6-dodecenoate.

* * * * *